US009060991B2

(12) United States Patent
Flatt et al.

(10) Patent No.: US 9,060,991 B2
(45) Date of Patent: Jun. 23, 2015

(54) USE OF GLP-1 ANALOGUES FOR THE TREATMENT OF DISORDERS ASSOCIATED WITH DYSFUNCTIONAL SYNAPTIC TRANSMISSION

(75) Inventors: Peter Raymond Flatt, Portrush (GB); Christian Holscher, Coleraine (GB); Victor Alan Gault, Ballymoney (GB)

(73) Assignee: Innovation Ulster Limited, Coleraine (GB)

( * ) Notice: Subject to any disclaimer, the term of this patent is extended or adjusted under 35 U.S.C. 154(b) by 0 days.

(21) Appl. No.: 12/677,047

(22) PCT Filed: Sep. 8, 2008

(86) PCT No.: PCT/EP2008/007338
§ 371 (c)(1),
(2), (4) Date: Mar. 8, 2010

(87) PCT Pub. No.: WO2009/030499
PCT Pub. Date: Mar. 12, 2009

(65) Prior Publication Data
US 2010/0227816 A1    Sep. 9, 2010

(30) Foreign Application Priority Data
Sep. 7, 2007    (GB) .................................. 0717399.0

(51) Int. Cl.
*A01N 37/18* (2006.01)
*A61K 38/00* (2006.01)
*A61K 38/26* (2006.01)

(52) U.S. Cl.
CPC ...................................... *A61K 38/26* (2013.01)

(58) Field of Classification Search
None
See application file for complete search history.

(56) References Cited

FOREIGN PATENT DOCUMENTS

WO    WO03/011892 A2    2/2003

OTHER PUBLICATIONS

Gault V.A. and Hölscher, C. "GLP-1 Agonists Facilitate Hippocampal LTP and Reverse the Impairment of LTP Induced by Beta-Amyloid" European Journal of Pharmacology 2008 vol. 587: 112-117.
Hölscher, C. and Gault V. "Insulin-Like Agonists Reverse Detrimental Effects on Synaptic Activity Induced by Beta-Amyloid Fragments" Alzhiemer's and Dementia Poster Presentations P2-480 Jul. 2008 vol. 4(4(suppl. 1)): T515.
Hölscher, C. "New Strategies to Prevent Neurodegeneration in Alzhiemer's Disease Using Insulin-Like Drugs" QRD Newsletter Alzhiemer's Society Dec. 2007 XP-002505676: 1-4.
Iwai et al. "Glucagon-Like Peptide-1 Inhibits LPS-Induced IL-1β Production in Cultured Rat Astrocytes" Neuroscience Research 2006 vol. 55: 352-360.
Wan et al. "Glucagon-Like Peptide-1 Modulates Synaptic Transmission to Identified Pancreas-Projecting Vagal Motoneurons" Peptides 2007 vol. 28: 2184-2191.

*Primary Examiner* — Olga N Chernyshev
(74) *Attorney, Agent, or Firm* — Licata & Tyrrell P.C.

(57) ABSTRACT

The present invention relates to a peptide analogue of glucagon-like peptide-1 (7-36), which is useful to prophylactically prevent, improve, or reverse the diminished cognitive function associated with these types of disorders, by increasing (or sustaining) the LTP of synaptic transmission. Moreover, sustaining LTP may find utility in the prophylaxis of neurological disease by delaying the onset of impaired cognitive processes, and could serve as a treatment, not only for the diminished cognitive function caused by neurodegeneration, but also for the dysfunctional cognitive processes associated with trauma or age.

12 Claims, 11 Drawing Sheets

SEQ ID NO:1

HAEGTFTSDVSSYLEGQAAKEFIAWLVKGR
7 8 9                17                  27               36

SEQ ID NO:2

X₁X₂X₃GTFTSDVSSYLEGQAAKEFIAWLVKGR
7 8 9                17                  27               36

SEQ ID NO:3

DAEGTFTSDVSSYLEGQAAKEFIAWLVKGR
7 8 9                17                  27               36

SEQ ID NO:4

HVEGTFTSDVSSYLEGQAAKEFIAWLVKGR
7 8 9                17                  27               36

SEQ ID NO:5

HAPGTFTSDVSSYLEGQAAKEFIAWLVKGR
7 8 9                17                  27               36

SEQ ID NO:6

HAEGTFTSDVSSYLEGQAAKEFIAWLVRGRG
7 8 9                17                  27               37

Figure 1

SEQUENCE LISTING

```
<160> NUMBER OF SEQ ID NOS: 6

<210> SEQ ID NO 1
<211> LENGTH: 30
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 30
<212> TYPE: PRT
<213> ORGANISM: Artificial sequence
<220> FEATURE:
<223> OTHER INFORMATION: Synthetic peptide analogue derived from human
      GLP-1
<220> FEATURE:
<221> NAME/KEY: MISC_FEATURE
<222> LOCATION: (1)..(3)
<223> OTHER INFORMATION: Xaa denotes any naturally occurring amino acid

<400> SEQUENCE: 2

Xaa Xaa Xaa Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 3
<211> LENGTH: 30
<212> TYPE: PRT
<213> ORGANISM: Artificial sequence
<220> FEATURE:
<223> OTHER INFORMATION: Synthetic peptide analogue derived from human
      GLP-1

<400> SEQUENCE: 3

Asp Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 30
<212> TYPE: PRT
<213> ORGANISM: Artificial sequence
<220> FEATURE:
<223> OTHER INFORMATION: Synthetic peptide analogue derived from human
      GLP-1

<400> SEQUENCE: 4

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
```

```
                        20                  25                  30

<210> SEQ ID NO 5
<211> LENGTH: 30
<212> TYPE: PRT
<213> ORGANISM: Artificial sequence
<220> FEATURE:
<223> OTHER INFORMATION: Synthetic peptide analogue derived from human
      GLP-1

<400> SEQUENCE: 5

His Ala Pro Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 31
<212> TYPE: PRT
<213> ORGANISM: Artificial sequence
<220> FEATURE:
<223> OTHER INFORMATION: Synthetic peptide analogue derived from human
      GLP-1

<400> SEQUENCE: 6

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```

USE OF GLP-1 ANALOGUES FOR THE TREATMENT OF DISORDERS ASSOCIATED WITH DYSFUNCTIONAL SYNAPTIC TRANSMISSION

This application is the U.S. National Phase of PCT/EP2008/007338 filed Sep. 8, 2008, which claims the benefit of priority of United Kingdom Serial No. 0717399.0 filed Sep. 7, 2007.

BACKGROUND

Glucagon-like Peptide-1 (GLP-1) is derived from the transcription product of the proglucagon gene, which in humans is known to be expressed in the pancreas and small intestine. Expression of proglugagon in pancreatic a cells results in the 29-amino acid glucagon peptide, glucagon related pancreatic peptide (GRPP), and the major proglucagon fragment. However, in intestinal endocrine cells, glucagon related pancreatic peptide (GRPP), oxyntomodulin, GLP-1, and GLP-2 are synthesized from the proglucagon gene. The 30-amino acid endogenous GLP-1 peptide belongs to the incretin family of hormones, and plays multiple roles in metabolic homeostasis following nutrient absorption. The major source of GLP-1 in the body is the intestinal L-cell, which secretes GLP-1 as a gut hormone in response to nutrient ingestion. GLP-1 secretion by L-cells is dependent on the presence of nutrients in the lumen of the small intestine. The secretagogues of this hormone include major nutrients such as carbohydrate, protein and lipid. The biologically active forms of GLP-1 are GLP-1(7-37) and GLP-1(7-36)amide. The biological activities of GLP-1 include inhibition of glucagon secretion from the pancreas, gastric emptying, and inhibition of food intake by increasing satiety. In particular, GLP-1 has modulating effects on insulin release. GLP-1 receptor stimulation enhances insulin biosynthesis, beta-cell proliferation, glucose-dependent insulin secretion from the pancreas, and lowers blood glucose in patients with type-2 diabetes mellitus (Gault et al., 2003). The finding that GLP-1 lowers blood glucose in patients with diabetes, taken together with suggestions that GLP-1 may restore beta-cell sensitivity to exogenous secretagogues, suggests that augmenting GLP-1 signalling is a useful strategy for treatment of diabetic patients.

Neuroplasticity is a process that involves the continual formation of new neural connections, and which occurs during the (re-)organisation of the brain in response to activity and experience. Activity-dependent synaptic plasticity plays a vital role in sculpting synaptic connections during development. However, although well known to occur during development, the process is also a central feature of the adult brain. The plastic nature of neuronal connections allows the brain to continually develop in response to experience, and to circumvent the impaired neuronal signalling that occurs as a consequence of trauma or damage to neurons.

There are two types of modifications that are thought to occur in the brain during this process: 1) morphological changes to the neurons themselves, specifically in the area of the synapse; and 2) an increase in the number of synapses between neurons. The efficiency of synaptic signalling is often dependent on either (or both) of these modifications. Indeed, it is widely accepted that processes such as memory formation and learning ability are dependent on alterations in synaptic efficiency that permit strengthening of associations between neurons. Moreover, synaptic plasticity at certain synapses is thought to be both necessary and sufficient for the process of storing information in the brain.

Long-term potentiation (LTP) has long been proposed as a model for the mechanism by which the strengthening of synaptic connections can be achieved. It has been widely demonstrated that high-frequency stimulation can cause a sustained increase in efficiency of synaptic transmission. Based on this finding, it is believed that the synaptic changes that underpin at least certain forms of learning and memory are similar to those changes required for expression of LTP.

Furthermore, it is widely accepted that impaired LTP is often associated with impaired cognitive function. In this regard, for a number of years now, studies have reported cognitive deficits in aged rats. In particular, aged rats have been shown to exhibit deficits in spatial information processing. Correlated with deficits in performance in spatial learning, was a deficit in LTP in the CA1 region of the rodent brain; wherein severely impaired animals did not sustain LTP, whilst sustained LTP was observed in those animals that were relatively unimpaired in spatial learning.

Therefore, cognitive deficits are a hallmark of a number of neurological disorders. For example, the symptoms of age-related memory impairment are often similar to those symptoms associated with the early stages of neurodegenerative diseases such as Alzheimer's disease. Clearly, a major goal in the field of neuroscience is to sustain LTP in circumstances where LTP is impaired, either by age, disease-associated causes, or by any other instance resulting in impaired synaptic transmission.

However, there is growing evidence that mature neurons may also possess mechanisms to prevent the strengthening of input synapses. Such homeostatic regulation ensures that a neuron operates within an optimal activity range, a process that is integral to maintaining the highly plastic nature of the brain. This is evident in the hippocampus, where pyramidal cells of the CA1 region each receive thousands of excitatory inputs with the potential for activity-dependent enhancement of synaptic transmission. In the absence of a mechanism to limit synaptic strengthening, the physiological balance can be compromised, resulting in the LTP process being shut down, and ultimately leading to a reduced capacity of the entire neuronal circuit for storing information. Therefore, the process of depotentiation also acts as a critical mediator in regulating neuronal homeostasis and ensuring the coordinated control of the strength of synaptic transmission. Depotentiation is now thought to play a role in the removal of redundant information from the memory. As such, depotentiation could act as a potential therapeutic measure in disorders associated with overactive cognitive processes.

It is an object of the present invention to prophylactically prevent, improve, or reverse the diminished cognitive function associated with these types of disorders, by increasing (or sustaining) the LTP of synaptic transmission. Moreover, sustaining LTP may find utility in the prophylaxis of neurological disease by delaying the onset of impaired cognitive processes, and could serve as a treatment, not only for the diminished cognitive function caused by neurodegeneration, but also for the dysfunctional cognitive processes associated with trauma or age.

SUMMARY OF THE INVENTION

According to a first aspect of the present invention, there is provided use of a peptide analogue of glucagon-like peptide-1 (7-36) for the treatment and prophylaxis of neurological disorders caused by, or associated with, dysfunction of long-term potentiation of synaptic transmission; the amino acid sequence of the peptide analogue comprising at least the first 10 amino acids from the N-terminal end of the sequence identified in SEQ ID NO: 1; and further comprising one or more amino acid substitutions or modifications selected from the group comprising, but not limited to, an amino acid substitution or modification at position 7, an amino acid substitution or modification at position 8, an amino acid substitution or modification at position 9, an amino acid substitution or modification at position 26, and an amino acid substitution or modification at position 34; with the proviso that, if there is a single amino acid substitution at position 8, then $X_2$ is not L-Ala or L-Gly.

According to a second aspect of the present invention, there is provided use of a peptide analogue, the amino acid sequence of the peptide analogue comprising at least the first 10 amino acids from the N-terminal end of the sequence identified in SEQ ID NO: 1; and further comprising one or more amino acid substitutions or modifications selected from the group comprising, but not limited to, an amino acid substitution or modification at position 7, an amino acid substitution or modification at position 8, an amino acid substitution or modification at position 9, an amino acid substitution or modification at position 26, and an amino acid substitution or modification at position 34; with the proviso that, if there is a single amino acid substitution at position 8, then X is not L-Ala or L-Gly, for the manufacture of a medicament for the treatment and prophylaxis of neurological disorders caused by, or associated with, dysfunction of long-term potentiation of synaptic transmission.

According to a third aspect of the present invention, there is provided a method of treating neurological disorders caused by, or associated with, dysfunction of long-term potentiation of synaptic transmission; wherein the method comprises the administration of a pharmaceutically acceptable amount of a peptide analogue, the amino acid sequence of the peptide analogue comprising at least the first 10 amino acids from the N-terminal end of the sequence identified in SEQ ID NO: 1; and further comprising one or more amino acid substitutions or modifications selected from the group comprising, but not limited to, an amino acid substitution or modification at position 7, an amino acid substitution or modification at position 8, an amino acid substitution or modification at position 9, an amino acid substitution or modification at position 26, and an amino acid substitution or modification at position 34; with the proviso that, if there is a single amino acid substitution at position 8, then X is not L-Ala or L-Gly, to a subject suffering from a neurological disorder caused by, or associated with, dysfunctional long-term potentiation of synaptic transmission.

Optionally, the amino acid sequence of the peptide analogue comprises at least the first 10 amino acids from the N-terminal end of the sequence identified in SEQ ID NO: 1; and further comprising one or more amino acid substitutions or modifications selected from the group comprising, but not limited to, an amino acid substitution or modification at position 26, and an amino acid substitution or modification at position 34.

Optionally, the amino acid substitution or modification at position 26 is independently selected from the group comprising addition of an amino acid, and/or addition of an acyl radical, optionally a fatty acid. Further optionally, the amino acid is L- or D-Glu, and the fatty acid is a C-16 palmitoyl group.

Optionally or additionally, the amino acid substitution or modification at position 34 is L- or D-Arg.

Optionally, the peptide analogue is Arg(34)Lys(26)-(N-epsilon-(gamma-Glu)(N-alpha-hexadecanoyl))GLP-1(7-37), also known as Liraglutide. The amino acid sequence of Liraglutide is derived from the basic amino acid sequence as illustrated in SEQ ID NO: 6.

By the term "dysfunction" is meant any disturbance resulting in the abnormal functioning of a process, whereby the process no longer follows a conventional functional pattern. The abnormal functioning of the process involves impaired LTP, wherein the treatment comprises enhancement of LTP.

The peptide analogue of glucagon-like peptide-1 (GLP-1) optionally comprises a polypeptide with an amino acid sequence as shown in SEQ ID NO: 2, wherein $X_2$ comprises an L- or D-amino acid selected from the group including: Arg, Asn, Asp, Cys, Glu, Gln, His, Ile, Leu, Lys, Met, Phe, Pro, Ser, Thr, Trp, Tyr, and Val.

Preferably, the peptide analogue of glucagon-like peptide-1 (GLP-1) comprises a polypeptide with an amino acid sequence as shown in SEQ ID NO: 2, wherein $X_2$ comprises a hydrophobic L- or D-amino acid. Further preferably, $X_2$ comprises an aliphatic L- or D-amino acid. Most preferably, $X_2$ comprises L- or D-Val. Optionally, the peptide analogue comprises at least 10 amino acid residues from the N-terminal end of the sequence identified in SEQ ID NO: 2, and further comprises one or more amino acid substitutions or modifications selected from the group consisting of: an amino acid substitution or modification at position 7, and an amino acid substitution or modification at position 9.

Optionally, the peptide analogue of glucagon-like peptide-1 (GLP-1) comprises a polypeptide with an amino acid sequence as shown in SEQ ID NO: 2, wherein $X_1$ is selected from any naturally occurring amino acid. Further preferably, $X_1$ comprises L- or D-Asp, as illustrated in SEQ ID NO: 3.

Optionally, the peptide analogue of glucagon-like peptide-1 (GLP-1) comprises a polypeptide with an amino acid sequence as shown in SEQ ID NO: 2, wherein $X_2$ is selected from any naturally occurring amino acid. Further preferably, $X_2$ comprises L- or D-Val, as illustrated in SEQ ID NO: 4.

Optionally, the peptide analogue of glucagon-like peptide-1 (GLP-1) comprises a polypeptide with an amino acid sequence as shown in SEQ ID NO: 2, wherein $X_3$ is selected from any naturally occurring amino acid. Further preferably, $X_3$ comprises L- or D-Pro, as illustrated in SEQ ID NO: 5.

A fragment of the peptide analogue comprises at least 10 amino acid residues from the N-terminal end of the sequence identified in SEQ ID NO: 1, and further comprises one or more amino acid substitutions or modifications selected from the group comprising, but not limited to, an amino acid substitution or modification at position 7, an amino acid substitution or modification at position 8, an amino acid substitution or modification at position 9, an amino acid substitution or modification at position 26, and an amino acid substitution or modification at position 34; with the proviso that, if there is a single amino acid substitution at position 8, then $X_2$ is not L-Ala or L-Gly.

The peptide analogue of GLP-1 is optionally an analogue of human GLP-1.

Preferably, the peptide analogue is resistant to degradation by dipeptidyl peptidase IV (DPP IV).

Optionally, the peptide analogue further comprises at least one amino acid modification, said at least one amino acid substitution or modification comprising attachment of a polymer moiety of the general formula HO—(CH$_2$—O—CH$_2$)$_n$—H, in which n is an integer between 1 and about 22.

Optionally, the polymer moiety has an average molecular weight of no more than 1000 Da. Preferably, the polymer moiety has an average molecular weight of less than 1000 Da.

Preferably, n is an integer between 1 and about 10. More preferably, n is an integer between about 2 and about 5.

Optionally, the polymer moiety has a branched structure. The branched structure may comprise the attachment of at least two polymer moieties of linear structure. Alternatively, the branch point may be located within the structure of each polymer moiety. Alternatively, the polymer moiety has a linear structure.

Some or all monomers of the polymer moiety can be associated with water molecules. Attachment of the polymer moiety can be achieved via a covalent bond. Optionally, the covalent bond is a stable covalent bond. Alternatively, the covalent bond is reversible. The covalent bond can be hydrolysable.

The or each polymer moiety can be attached adjacent the N-terminal amino acid of the peptide analogue; adjacent the C-terminal amino acid of the peptide analogue; or to a naturally occurring amino acid selected from the group including, but not limited to, lysine, cysteine, histidine, arginine, aspartic acid, glutamic acid, serine, threonine, and tyrosine. Alternatively, the peptide analogue further comprises substitution of a naturally occurring amino acid with an amino acid selected from the group including, but not limited to, lysine, cysteine, histidine, arginine, aspartic acid, glutamic acid, serine, threonine, and tyrosine; the or each polymer moiety being attached to the or each substituted amino acid. Optionally, the or each polymer moiety is attached adjacent the C-terminal amino acid. Further optionally, the or each polymer moiety is attached to the C-terminal amino acid.

Optionally, the or each polymer moiety is attached to a lysine residue. The or each polymer moiety can be attached to the alpha or epsilon amino groups of lysine. The lysine residue can be chosen from the group consisting of Lys(26), and Lys(34).

As used throughout, the term "mini-PEG" (or "mPEG") is intended to be synonymous with an attached polymer of polyethylene glycol as previously described herein in which n is an integer between 1 and about 22.

Optionally, the peptide analogue comprises an amino acid modification at position 7, wherein the amino acid modification is an acylation such as, but not limited to, an acetylation. The peptide analogue can be acylated (optionally acetylated) adjacent the N-terminus. Optionally, the peptide analogue is acylated (optionally acetylated) at the N-terminal alpha-amine.

Optionally, the peptide analogue comprises:
(a) N-terminal glycation and an amino acid substitution at one, two, or all of positions 7, 8 and 9;
(b) amino acid substitution and/or modification at each of positions 7, 8 and 9; and
(c) amino acid substitution and/or modification at one of positions 7, 8, and 9; wherein the amino acid substitution or modification is selected from the group consisting of:
  (i) glycation at position 7, 8, or 9;
  (ii) alkylation at position 7, 8, or 9;
  (iii) acetylation at position 7, 8, or 9;
  (iv) acylation at position 7, 8, or 9;
  (v) the addition of an isopropyl group at position 7, 8, or 9;
  (vi) the addition of a pyroglutamic acid at position 7, 8, or 9;
  (vii) substitution at position 7 by a D-amino acid;
  (viii) substitution at position 7 by an L-amino acid;
  (ix) substitution at position 8 by an L-amino acid, with the proviso that, the L-amino acid is not L-Ala or L-Gly;
  (vii) substitution at position 9 by a D-amino acid;
  (x) substitution at position 9 by an L-amino acid;
  (xi) substitution at position 7, 8, or 9 by amino isobutyric acid or sarcosine;
  (xii) substitution at position 8 by a D-amino acid;
  (xiii) conversion of the Ala(8)-Glu(9) bond to a ψ[CH$_2$NH] bond;
  (xiv) conversion of the Ala(8)-Glu(9) bond to a stable isostere bond;
  (xv) substitution at position 7, 8, or 9 by beta-alanine, an omega-amino acid, 3-amino propionic acid, 4-amino butyric acid, ornithine, citrulline, homoarginine, t-butylalanine, t-butylglycine, N-methylisoleucine, phenylglycine, and cyclohexylalanine, norleucine, cysteic acid and methionine sulfoxide;
(d) amino acid modification comprising the attachment of a polymer moiety of the general formula HO—(CH$_2$—O—CH$_2$)$_n$—H; and
(e) modification by acyl radical addition, optionally a fatty acid addition, at an epsilon amino group of an amino acid residue.

Optionally, the peptide analogue consists of 10 amino acids from the N-terminal end of the sequence identified in SEQ ID NO: 2. Preferably, the peptide analogue retains the biological activity of GLP-1(7-37) and GLP-1(7-36)amide.

Optionally, the peptide analogue comprises a modification comprising addition of at least one acyl radical, optionally a fatty acid molecule, at an amino group of at least one amino acid residue. Optionally, the or each fatty acid molecule is attached to a lysine residue. The or each fatty acid molecule can be attached to the alpha or epsilon amino groups of lysine. The lysine residue can be chosen from the group consisting of Lys(26), and Lys(34).

Optionally, the fatty acid is a saturated fatty acid. Further optionally, the modification comprises the addition of a fatty acid selected from the group comprising, but not limited to, a C-8 octanoyl group, a C-10 decanoyl group, a C-12 lauroyl group, a C-14 myristoyl group, a C-16 palmitoyl group, a C-18 stearoyl group, or a C-20 acyl group.

Preferably, the peptide analogue comprises an N-glycated amino acid at position 7. Further preferably, the peptide analogue comprises an N-glycated His residue at position 7.

Optionally, the peptide analogue comprises an N-alkylated amino acid at position 7. Further optionally, the peptide analogue comprises the addition of an N-terminal isopropyl group at position 7. Further optionally, the peptide analogue comprises the addition of an N-terminal pyroglutamic acid at position 7. Further optionally, the peptide analogue further comprises a modification by fatty acid addition at an epsilon amino group of at least one lysine residue, and an amino acid substitution or modification at one, two, or all of positions 7, 8, and 9.

Preferably, the amino acid substitution at position 7 results in an Asp residue. Preferably, the amino acid substitution at position 8 results in a Val residue. Preferably, the amino acid substitution at position 9 results in a Pro residue.

Optionally, the peptide analogue further comprises a modification comprising addition of at least one amino acid at an amino group of at least one amino acid residue. Preferably, the added amino acid is a Glu. Optionally, the or each amino acid is attached to a lysine residue. The or each amino acid can be attached to the alpha or epsilon amino groups of lysine. The lysine residue can be chosen from the group consisting of Lys(26), and Lys(34).

According to a still further aspect of the present invention there is provided the use of Liraglutide for the treatment and prophylaxis of neurological disorders caused by, or associated with, dysfunction of long-term potentiation of synaptic transmission.

For the purposes of the present specification, it is understood that this invention is not limited to the specific methods, treatment regimens, or particular procedures, which as such may vary. Moreover, the terminology used herein is for the purpose of describing particular embodiments and is not intended to be limiting.

As used throughout, the term "glucagon-like peptide-1" (or "GLP-1") is intended to be synonymous with full length GLP-1, GLP-1(7-36), and GLP-1(7-36)amide. Preferably, the term refers to human GLP-1.

The term "polypeptide" is used herein synonymously with the term peptide.

By the term "subject", is meant an individual. Preferably, the subject is a mammal. More preferably, the subject is a human.

For the purposes of this specification, it is understood that position 7 refers to the N-terminal amino acid of the peptide analogue, and that the amino acid positions described herein are synonymous with the amino acid positions as illustrated in the accompanying drawings.

BRIEF DESCRIPTION OF THE DRAWINGS

An embodiment of the invention will now be described, by way of example with reference to the accompanying drawings, in which:

FIG. 1 illustrates the polypeptide sequences of human GLP-1(7-36) (SEQ ID NO: 1), and peptide analogues of GLP-1 (SEQ ID NOs: 2-5);

MATERIALS AND METHODS

Surgery and LTP Induction Protocols

Figure 2:
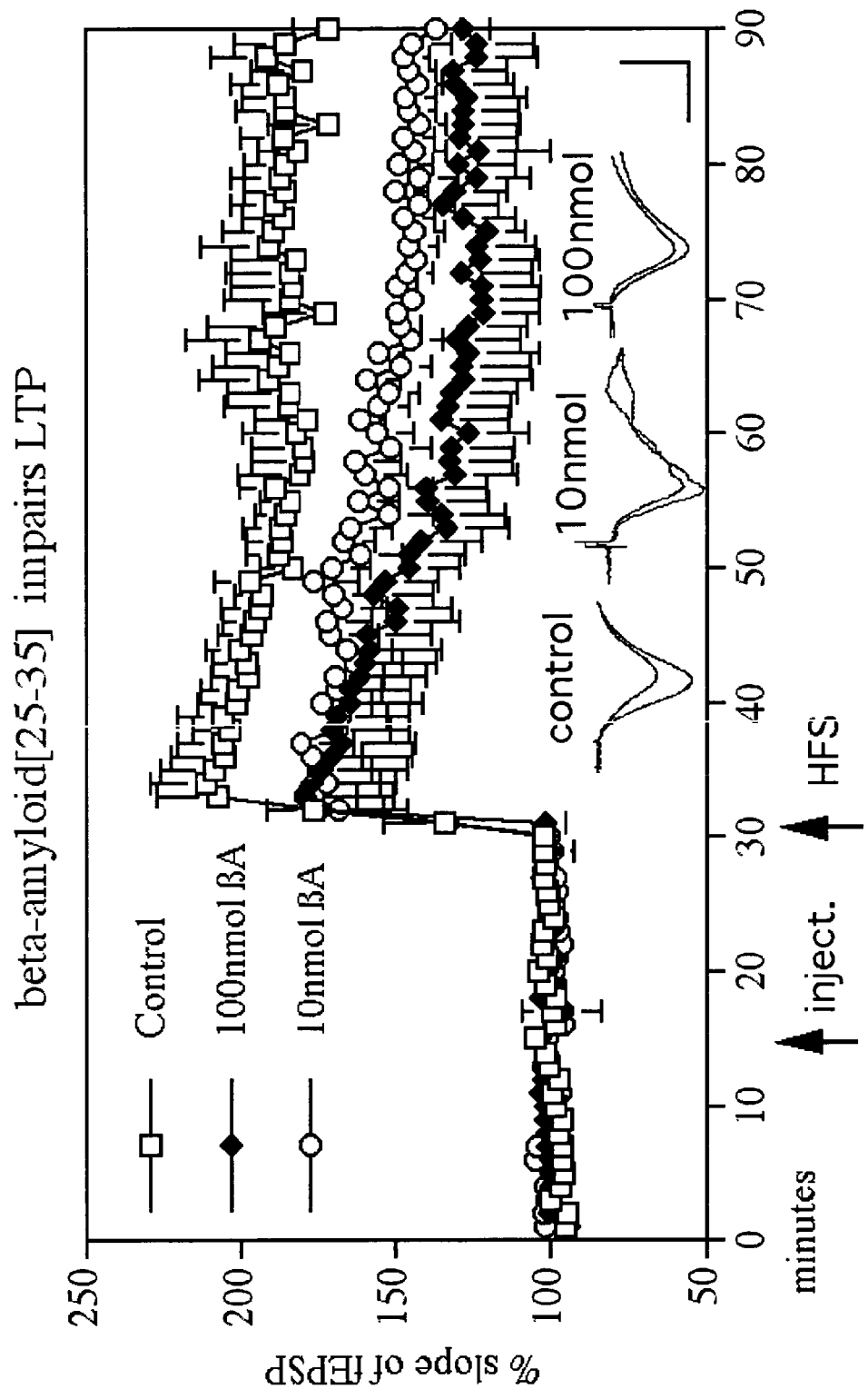
FIG. 2 illustrates the effect of beta-amyloid(25-35) on long-term potentiation of synaptic transmission.

Male Wistar rats weighing 220-280 g were anaesthetised with urethane (ethyl carbamate, 1.8 g/kg, intraperitoneal, (i.p.)) for the duration of all experiments. The animals had been obtained from Harlan, United Kingdom (UK). A cannula (22 gauge, 0.7 mm outer diameter, 11 mm in length, Bilaney, Kent, UK) was implanted (1.5 mm anterior to bregma, 0.5 mm lateral to the midline and 3.55 mm ventral) into the left hemisphere for intracerebroventricular (icv) injections. Electrodes (tungsten with Teflon® coating, Bilaney, Kent, UK) were implanted unilaterally 3.4 mm posterior and 2.5 mm lateral to the midline, and the stimulating electrode 4.2 mm posterior to bregma and 3.8 mm lateral to the midline. The electrodes were slowly lowered through the cortex and the upper layers of the hippocampus and into the CA1 region until the appearance of a negative deflecting excitatory post-synaptic potential (EPSP) that had a latency of ca. 10 ms. Recordings of EPSPs were made from the stratum radiatum in the CA1 region of the right hippocampal hemisphere in response to stimulation of the Schaffer collateral/commissural pathway. Field EPSPs were recorded on a computerised stimulating and recording unit (PowerLab, ADI instruments, UK) in which the trigger threshold was adjustable. The triggered unit activated a constant current stimulus isolation unit (Neurolog, UK). The data acquisition system was triggered simultaneously to record all events. Sampling speed was at 20 kHz recording of EPSPs.

The 'strong' high frequency stimulation (HFS) protocol for inducing long-term potentiation (LTP) consisted of 3 trains of 200 stimuli, inter-stimulus interval 5 ms (200 Hz), inter-train interval 2 sec. This standard HFS has been shown to induce maximal LTP under these recording conditions (Hölscher et al., 1997). The 'weak' HFS protocol for inducing LTP consisted of 10 trains of 10 stimuli, inter-stimulus interval 5 ms (200 Hz). The strong HFS was used to test the effects of peptides that impair LTP (beta-amyloid), and the weak HFS was used to test peptides that facilitate LTP. In this form of LTP, the control group is not potentiated at a maximal rate, and LTP can decay slowly over time. Stimulation intensity was 70% of the maximum EPSP. LTP was measured as % of baseline EPSP slope recorded over a 30 min period prior to drug injection and 60 min prior to application of HFS. Baseline was recorded for 30 min and averaged. This value was taken as 100% of the EPSP slope and all recoded values were normalised to this baseline value. All experiments were licensed according to UK Home Office regulations, and the "Principles of laboratory animal care" (NIH publication No. 86-23, revised 1985) were followed.

Peptides

Beta-amyoid (25-35) and other peptides used in this study were synthesised on an Applied Biosystems automated peptides synthesiser (Model 432A) using standard solid-phase Fmoc protocols. Peptides were judged pure by reversed phase HPLC on a waters Millenium 2010 chromatography system, and peptides were subsequently characterised using matrix-assisted laser desorption/ionisation time of flight (MALDI-TOF) mass spectrometry as described previously (Gengler et al., 2006; Hölscher et al., 2007). Peptides were stored in dry form and dissolved in double distilled water before the experiments. 5 μl of peptides solution was injected icv.

Statistics

Each group consisted of 6 animals. Data were analysed using a repeated measures two-way ANOVA, or a repeated measures three level two-way ANOVA with post-hoc tests to discriminate between groups (PRISM, GraphPad software Inc; USA).

EXAMPLES

The following examples are described herein so as to provide those of ordinary skill in the art with a complete disclosure and description of the invention, and are intended to be purely exemplary of the present invention, and are not intended to limit the scope of the invention.

Example 1

Peptide Sequence

The amino acid sequences of human GLP-1, and analogues thereof, are given in FIG. 1. The amino acids are numbered below.

SEQ ID NO: 1 illustrates the amino acid sequence of human GLP-1;

SEQ ID NO: 2 illustrates the amino acid sequence of an analogue of human GLP-1, which is modified by an amino acid substitution at position 7 (indicated by $X_1$), position 8 (indicated by $X_2$), and/or position 9 (indicated by X3);

SEQ ID NO: 3 illustrates the amino acid sequence of the analogue Asp(7)GLP-1;

SEQ ID NO: 4 illustrates the amino acid sequence of the analogue Val(8)GLP-1;

SEQ ID NO: 5 illustrates the amino acid sequence of the analogue Pro(9)GLP-1; and SEQ ID NO: 6 illustrates the amino acid sequence of the analogue Liraglutide.

Example 2

In vivo Effects of Beta-amyloid(25-35) Treatment

Male Wistar rats were intracerebroventricularly (icv) injected with either an inactive scrambled peptide sequence version of beta-amyloid (βA)(25-35) (Control,) 10 nmol (O) or 100 nmol (♦) βA(25-35). LTP was induced 15 min post-injection using the HFS (strong protocol), and the change in EPSP assessed and graphed to represent the change in LTP (FIG. 2). A three level two-way repeated measures ANOVA found an overall difference between groups ($DF_{2,16}$; F=6.2, p<0.001) and time ($DF_{2,119}$; F=1.9; p<0.01). Interaction between factors was not significant. A two-level two-way repeated measures ANOVA showed a difference between the 100 nmol group and control ($DF_{1,10}$; F=16.1; p<0.005) and over time $DF_{1,119}$; F=1.5; p<0.001). Interaction between factors was not significant. A two-level two-way repeated measure ANOVA showed a difference between the 10 nmol group and control ($DF_{1,10}$; F=9.1; p<0.01) and over time $DF_{1,119}$; F=1.38; p<0.005). Interaction between factors was not significant. There was no difference between the 10 nmol and the 100 nmol group. N=6 per group. Averaged EPSPs are shown recorded 5 min pre-HFS and 1 h post-HFS. These EPSPs are examples to demonstrate the quality of the recording. As shown, the EPSPs clearly changed after stimulation and are of high quality with very little noise. Calibration bars are 10 ms horizontal, 1 mV vertical. All groups n=6.

These results demonstrate the detrimental effects of βA(25-35) on LTP. The underlying mechanisms of this impairment include the change of K+ channel activity, reduction of voltage-dependent calcium channel (VDCC) activity, and Ca2+ influx, which in turn affects Ca2+ sensitive enzyme activity, and reduces vesicle release. Interestingly, previous studies have shown that the release of beta-amyloid is affected and reduced by GLP-1.

Example 3

In vivo Effects of Treatment with GLP-1(7-36) Amide, GLP-1(9-36)Amide, and Val(8)GLP-1

Figure 3A:
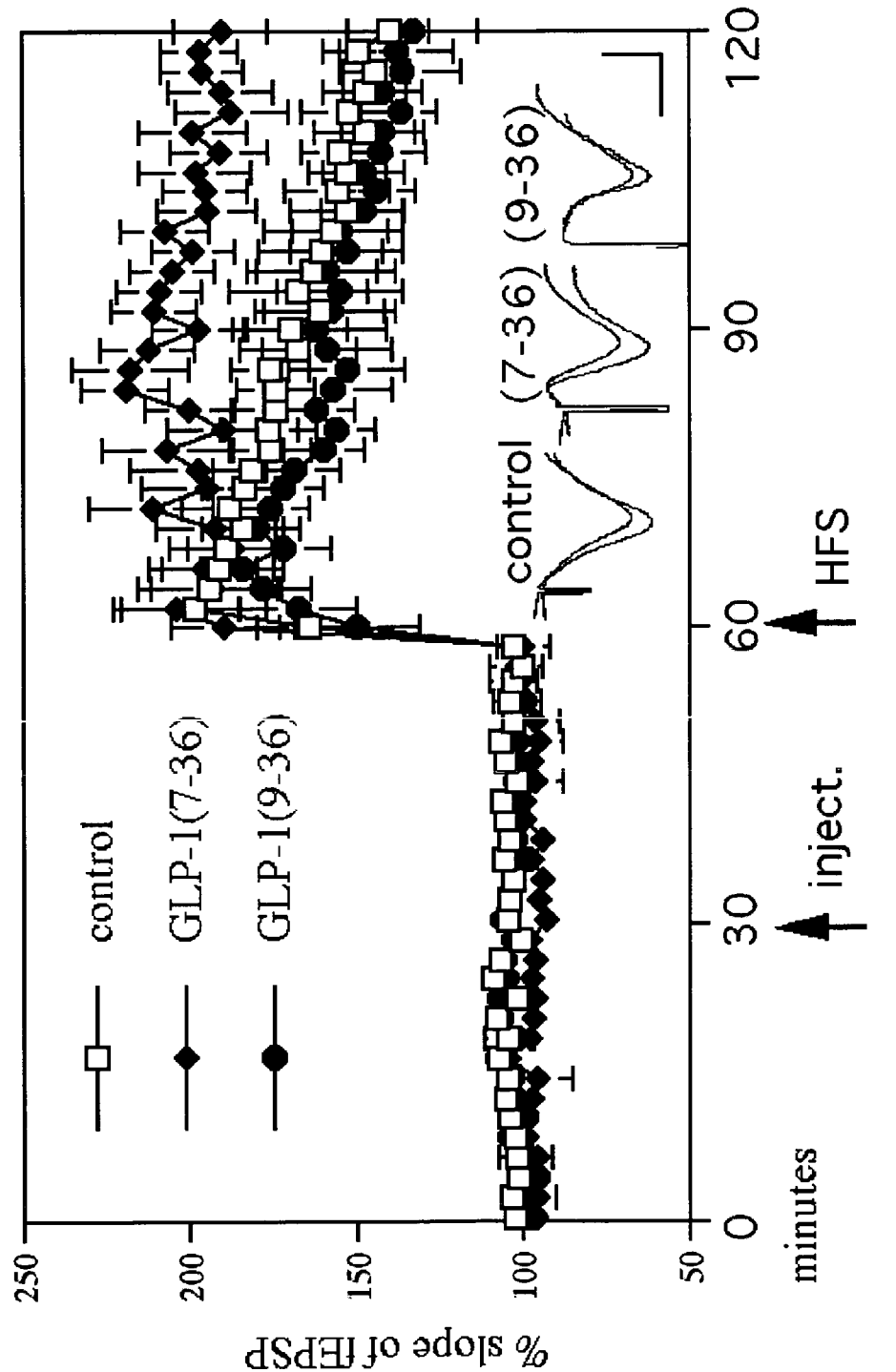
FIG. 3A illustrates the effect of GLP-1 on long-term potentiation of synaptic transmission.

The natural hormone GLP-1(7-36)amide was injected (15 nmol in 5 μl icv.) to test the effects on LTP using a weak stimulation protocol (FIG. 3A). In addition, an inactive form of GLP-1, GLP-1(9-36)amide, had been injected as a control (15 nmol in 5 μl icv.). A three level two-way repeated measures ANOVA found an overall difference between groups ($DF_{2,16}$; F=7.4, p<0.001) and time ($DF_{2,119}$; F=3.6; p<0.001). Interaction between factors was not significant. A two-level two-way repeated measures ANOVA showed a difference between the GLP-1(7-36)amide group and control ($DF_{1,10}$; F=12.1; p<0.01) and over time $DF_{1,119}$; F=1.6; p<0.001). Interaction between factors was not significant. A two-level two-way repeated measures ANOVA showed a difference between the GLP-1(7-36)amide group and the GLP-1(9-36) amide group ($DF_{1,10}$; F=12.1; p<0.01) and over time ($DF_{1,119}$, F=1.7; p<0.001). Interaction between factors was not significant. There was no difference between the GLP-1 (9-36)amide group and the control group. All groups n=6.

Figure 3B:
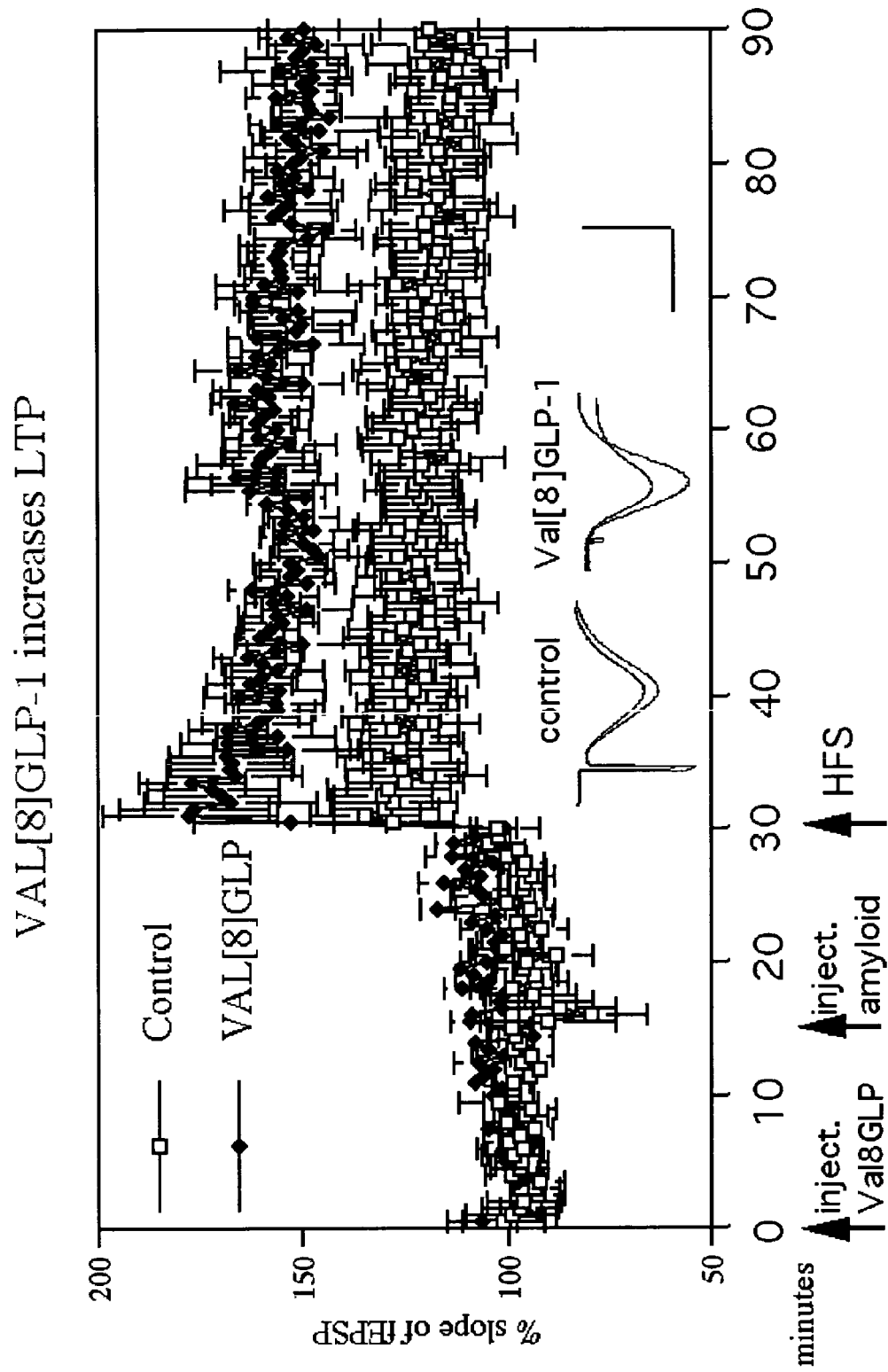
FIG. 3B illustrates the effect of Val(8)GLP-1 on long-term potentiation of synaptic transmission.

Male Wistar rats were icv injected with either vehicle (Control,) or 15 nmol Val(8)GLP-1 (♦). LTP was induced 30 min post-injection using the HFS (weak protocol), and the change in EPSP assessed and graphed to represent the change in LTP (FIG. 3B). A two-level two-way repeated measures ANOVA showed a difference between the Val(8)GLP-1 group and control ($DF_{1,10}$; F=17.1; p=0.003) and over time ($DF_{1,119}$, F=1.8; p=0.006). Interaction between factors was not significant. All groups n=6. Averaged EPSPs are shown recorded 5 min pre-tetanus and 1 h post-tetanus. These EPSPs are examples to demonstrate the quality of the recording. As shown, the EPSPs clearly changed after stimulation, and are of high quality with very little noise. Calibration bars are 10 ms horizontal, 1 mV vertical.

These results show for the first time that Val(8)GLP-1 has direct and acute modulating effects on synaptic transmission and can enhance the induction of LTP. This effect is different from effects observed after growth receptor activation, which have a much longer time course. Therefore, we interpret the results that the fast effects on LTP may be triggered by the activation of GLP-1 receptors on neurons, most likely at the pre-synaptic site where they could directly modulate vesicle release. Without being bound by theory, we postulate that the mechanism by which GLP-1 increases insulin release in the pancreas is similar to the effects on LTP and synaptic transmission observed in the present study in the brain.

Example 4

In vivo Effect of Val(8)GLP-1 and Beta-amyloid(25-35) Treatment

Figure 4A:
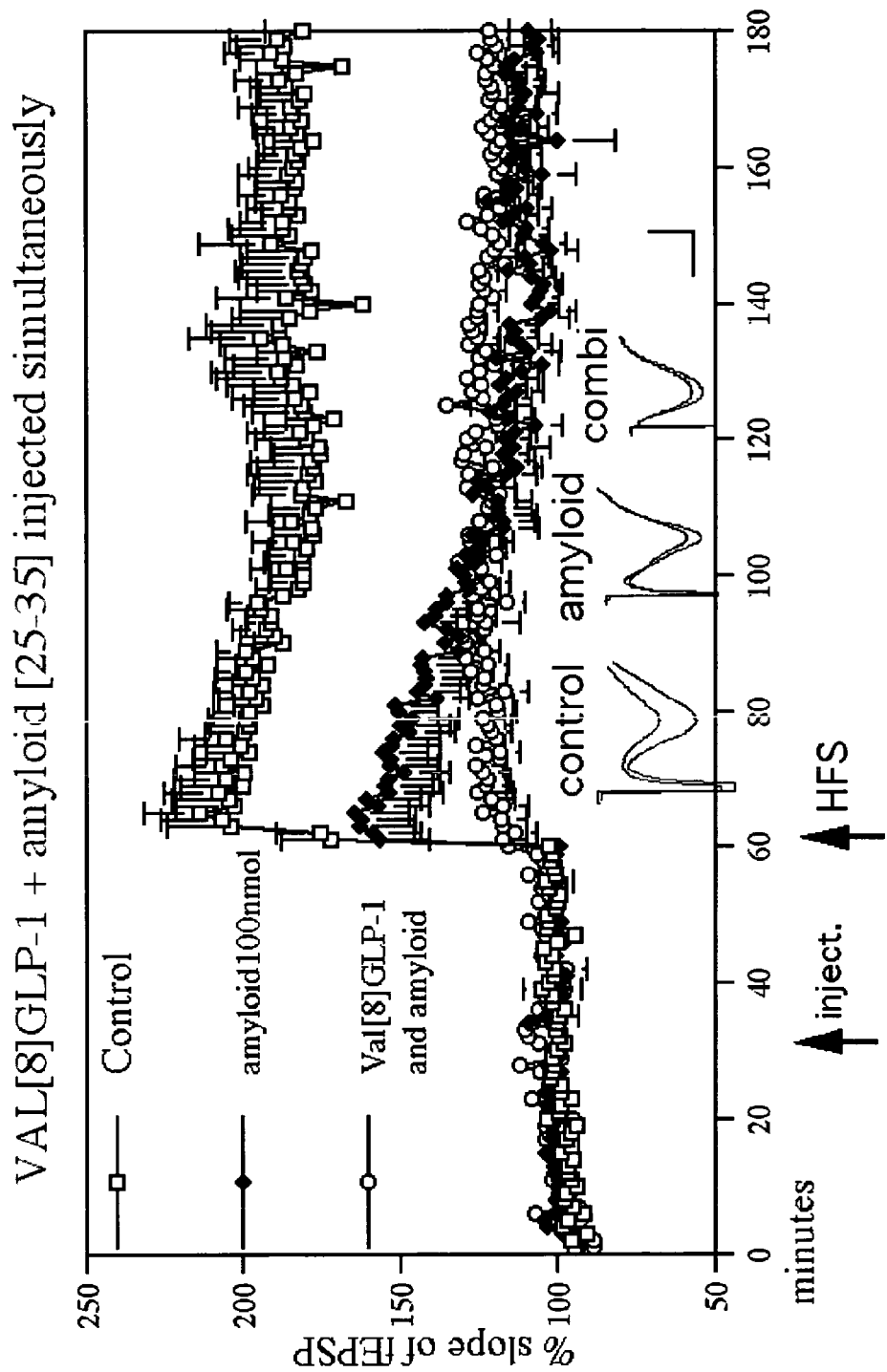
FIG. 4A illustrates the effect of co-administering Val(8) GLP-1 and beta-amyloid(25-35) on long-term potentiation of synaptic transmission.
Figure 4B:
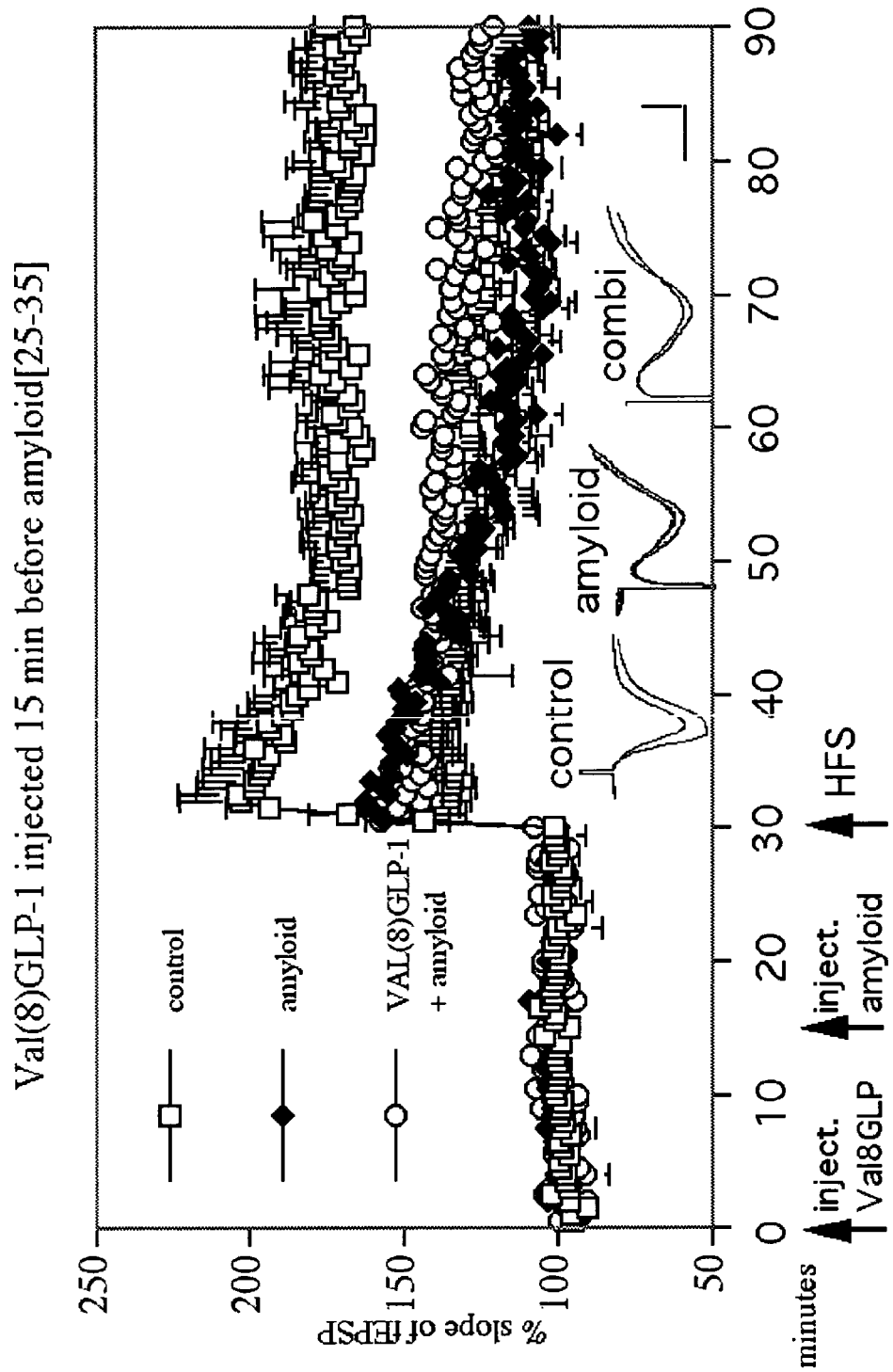
FIG. 4B illustrates the effect of administering Val(8)GLP-1 15 mins prior to beta-amyloid(25-35) on long-term potentiation of synaptic transmission.
Figure 4C:
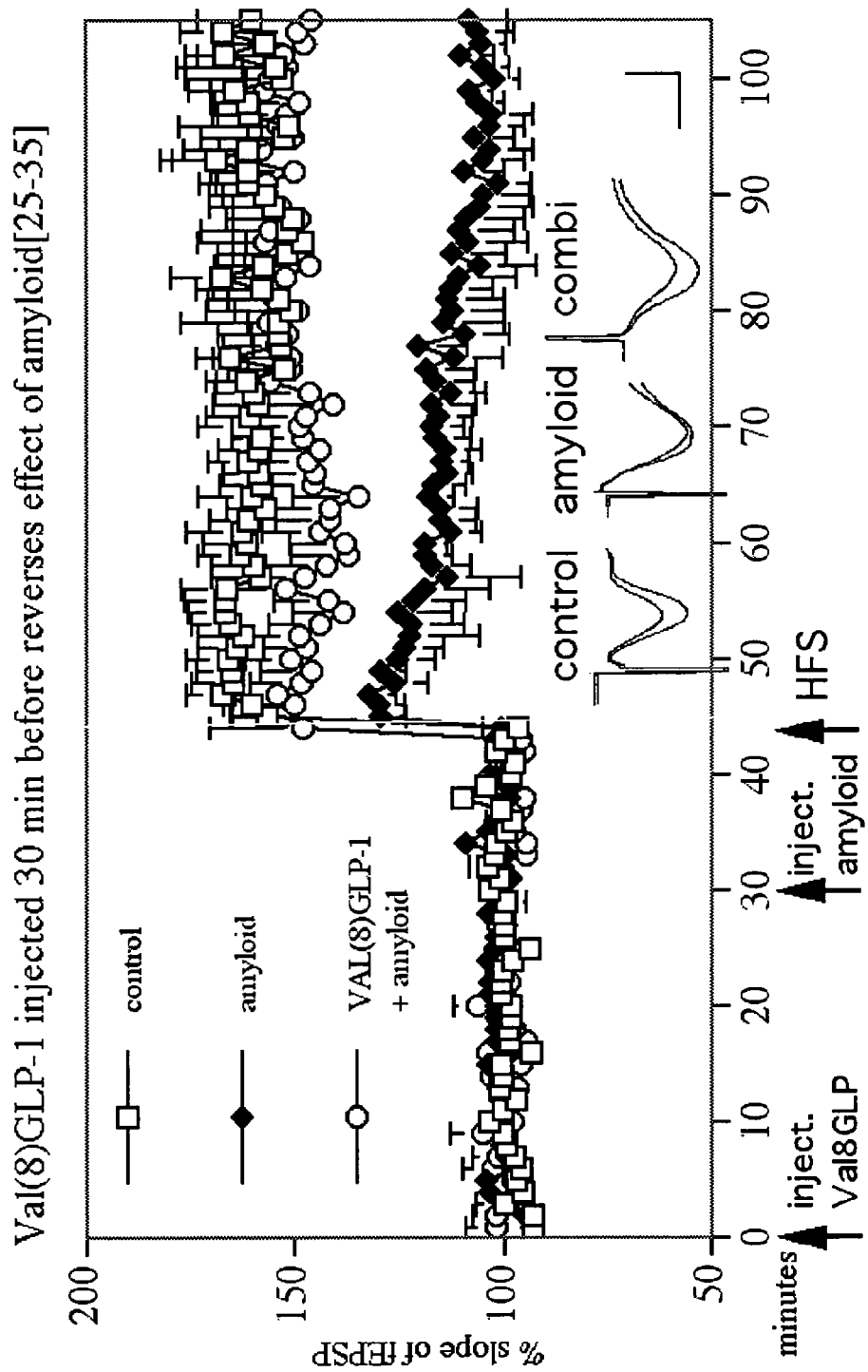
FIG. 4C illustrates the effect of administering Val(8)GLP-1 30 mins prior to beta-amyloid(25-35) on long-term potentiation of synaptic transmission.
Figure 5:
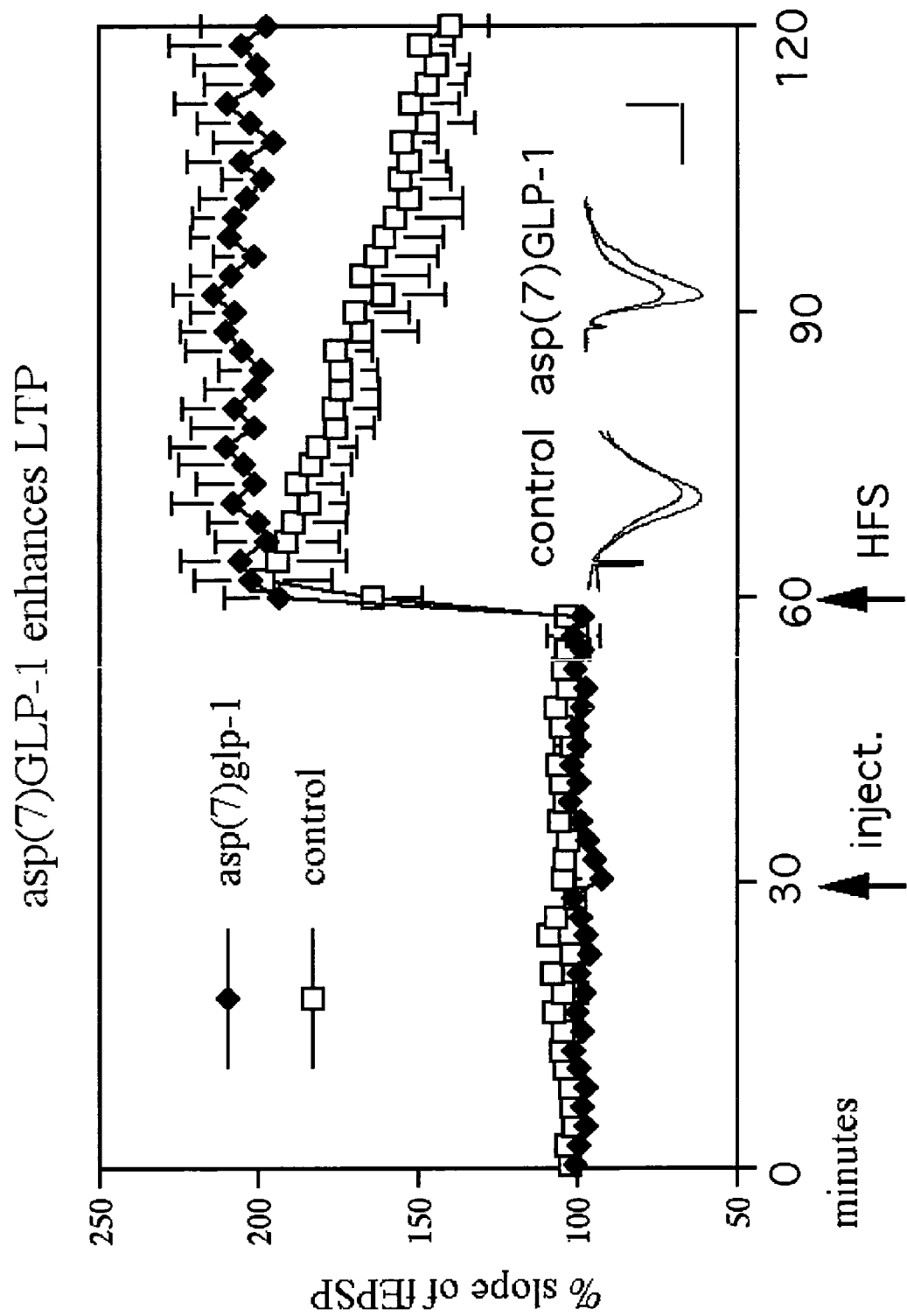
FIG. 5 illustrates the effect of Asp(7)GLP-1 on long-term potentiation of synaptic transmission.
Figure 6:
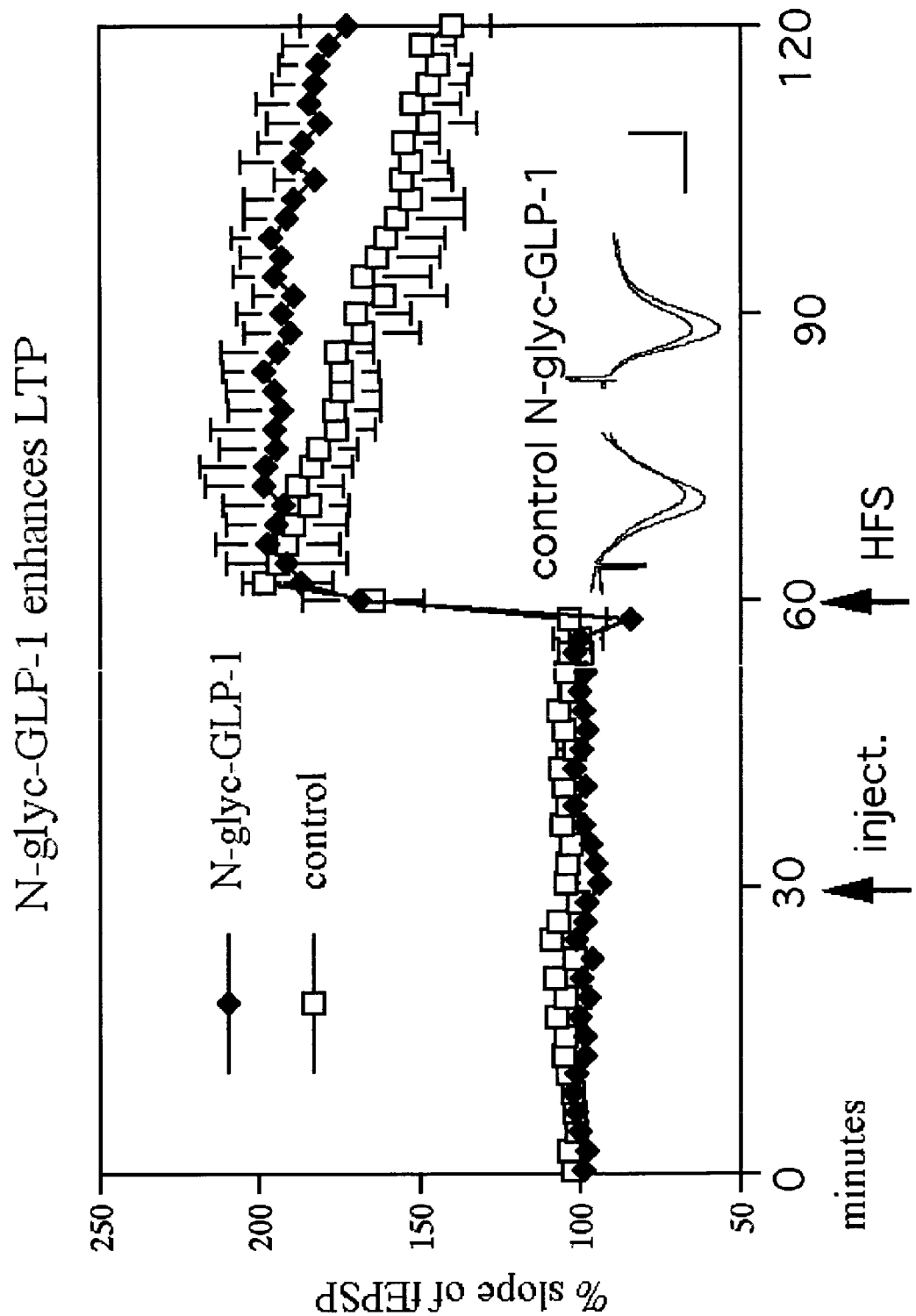
FIG. 6 illustrates the effect of [N-Glycated]GLP-1 on long-term potentiation of synaptic transmission.
Figure 7:
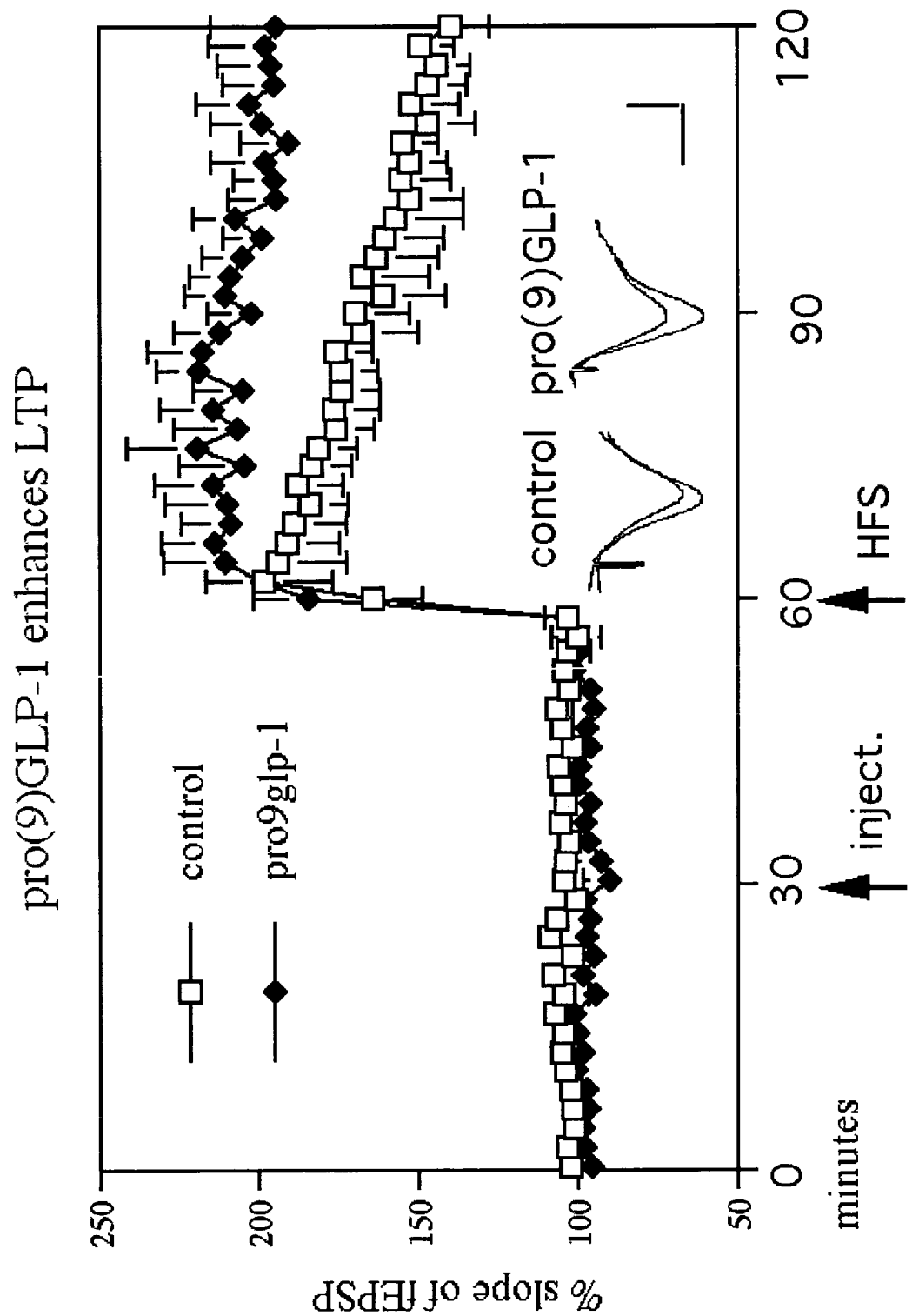
FIG. 7 illustrates the effect of Pro(9)GLP-1 on long-term potentiation of synaptic transmission.
Figure 8:
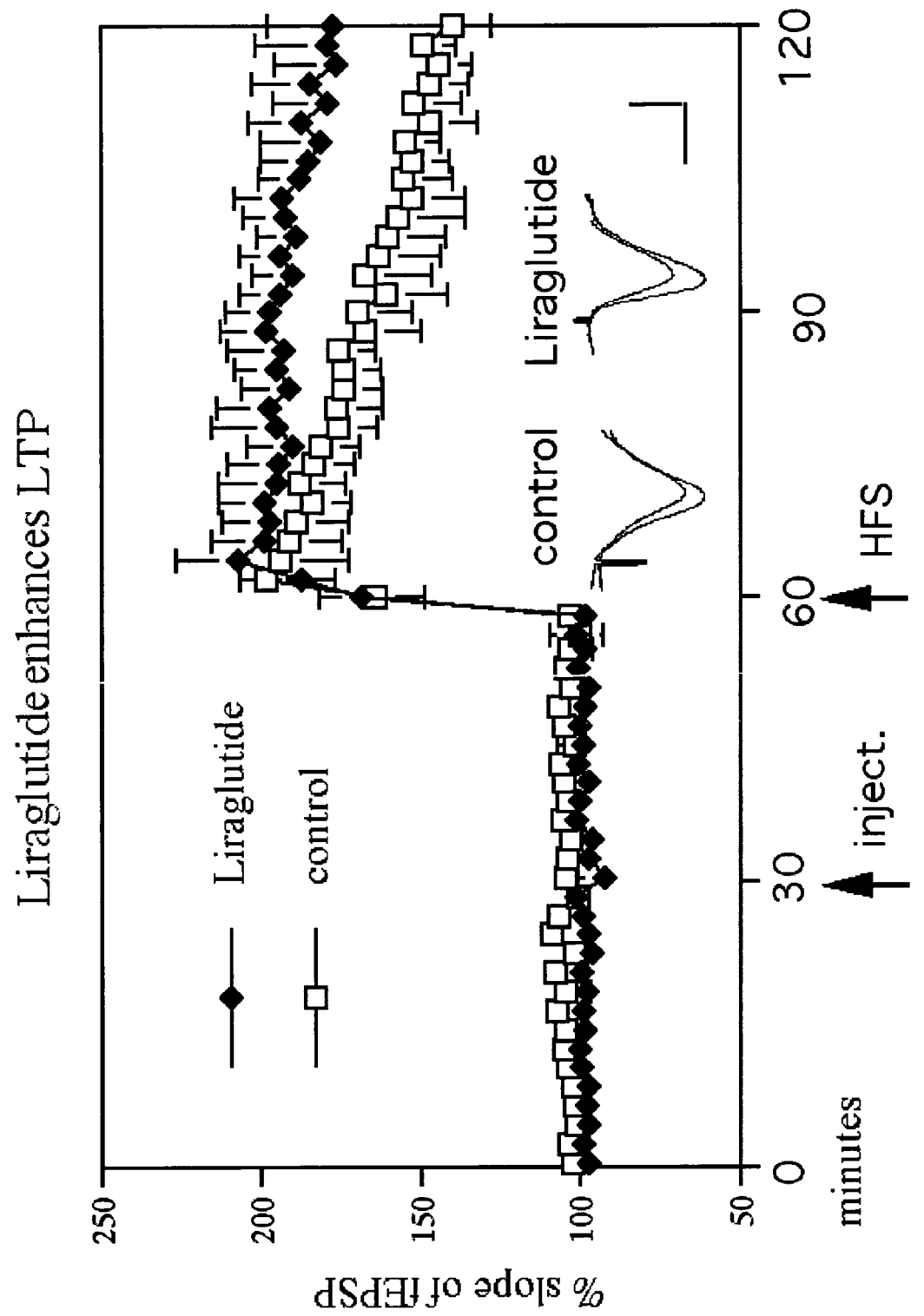
FIG. 8 illustrates the effect of Liraglutide on long-term potentiation of synaptic transmission.

Male Wistar rats were icv injected with either vehicle (Control,), 100 nmol βA(25-35) (♦), or a combination of 15 nmol Val(8)GLP-1 and 100 nmol βA(25-35) (O). βA(25-35) and Val(8)GLP-1 were injected simultaneously, and LTP was induced 15 min post-βA(25-35)-injection using the HFS (weak protocol), and the change in EPSP assessed and graphed to represent the change in LTP (FIG. 4A). Since this experiment was to test whether Val(8)GLP-1 can prevent the βA-induced impairment of LTP, a strong HFS protocol was used to obtain maximal LTP. Therefore, Val(8)GLP-1 was not tested on its own in this protocol, since LTP was already induced at maximal level and could not be enhanced further by Val(8)GLP-1. We have tested Val(8)GLP-1 on its own using a weak HFS protocol, which showed an enhancement of LTP (see Example 3). When injecting Val(8)GLP-1 (15 nmol in 5 μl icv) simultaneously with beta-amyloid(25-35) (100 nmol in 5 μl icv), the impairing effect of beta-amyloid on LTP was not affected. A three level two-way repeated measures ANOVA found an overall difference between groups ($DF_{2,16}$; F=3.9, p<0.0001) and over time ($DF_{2,119}$; F=16.5; p<0.001). Interaction was also significant ($DF_{2,240}$; F=1.8; p<0.001). A two-level two-way repeated measures ANOVA showed a difference between the beta-amyloid(25-35) group and control ($DF_{1,10}$; F=17.1; p<0.001) and over time ($DF_{1,119}$; F=4.5; p<0.001). No difference was found between the combination group and the beta-amyloid(25-35) group. All groups n=6.

βA(25-35) was injected 15 mins after Val(8)GLP-1, and LTP was induced 15 min post-βA(25-35)-injection using the HFS (weak protocol), and the change in EPSP assessed and graphed to represent the change in LTP (FIG. 4B). When injecting Val(8)GLP-1 (15 nmol in 5 µl icv) 15 min before beta-amyloid(25-35) (100 nmol in 5 µl icv), the impairing effect of beta-amyloid on LTP was not significantly affected, but a trend became visible. A three level two-way repeated measures ANOVA found an overall difference between groups ($DF_{2,16}$; F=6, p<0.01) and over time ($DF_{1,119}$; F=5.7; p<0.001). Interaction was also significant ($DF_{1,238}$; F=1.3; p<0.001). A two-level two-way repeated measures ANOVA showed a difference between the beta-amyloid(25-35) group and control ($DF_{1,10}$; F=11.3; p<0.01) and over time ($DF_{1,119}$; F=5.7; p<0.0001). No difference was found between the combination group and the beta-amyloid(25-35) group. All groups n=6.

βA(25-35) was injected 30 mins after Val(8)GLP-1, and LTP was induced 15 min post-βA(25-35)-injection using the HFS (weak protocol), and the change in EPSP assessed and graphed to represent the change in LTP (FIG. 4C). When injecting Val(8)GLP-1 (15 nmol in 5 µl icv) 30 min before beta-amyloid(25-35) (100 nmol in 5 µl icv), the impairing effect of beta-amyloid on LTP was completely reversed. A three level two-way repeated measures ANOVA found an overall difference between groups ($DF_{2,16}$; p<0.001) and over time ($DF_{1,119}$; F=3.8; p<0.001). A two-level two-way repeated measures ANOVA showed a difference between the beta-amyloid(25-35) group and control ($DF_{1,10}$; F=18; p<0.001) and over time ($DF_{1,119}$; F=1.8; p<0.001). No difference was found between the control group and the drug combination group. All groups n=6.

Example 5

In vivo Effects of Treatment with the GLP-1 Analogue, Asp(7)GLP-1

Male Wistar rats were icv injected with either vehicle (Control,) or 15 nmol D-Asp(7)GLP-1 (♦). LTP was induced 30 min post-injection using the HFS (weak protocol), and the change in EPSP assessed and graphed to represent the change in LTP. A two-way repeated measures ANOVA showed a difference between the drug group and control (p<0.001). All groups n=6. Averaged EPSPs are shown recorded 5 min pre-tetanus and 1 h post-tetanus. Calibration bars are 10 ms horizontal, 1 mV vertical.

Injection (icv) of 15 nmol Asp(7)GLP-1 enhanced long-term potentiation (LTP) compared with control. These results demonstrate that Asp(7)GLP-1 has direct and acute modulating effects on synaptic transmission and can enhance the induction of LTP.

Example 6

In vivo Effects of Treatment with the GLP-1 Analogue, [Nglyc]GLP-1

Male Wistar rats were icv injected with either vehicle (Control,) or 15 nmol D-Nglyc-GLP-1 (♦). LTP was induced 30 min post-injection using the HFS (weak protocol), and the change in EPSP assessed and graphed to represent the change in LTP. A two-way repeated measures ANOVA showed a difference between the drug group and control (p<0.01). All groups n=6. Averaged EPSPs are shown recorded 5 min pre-tetanus and 1 h post-tetanus. Calibration bars are 10 ms horizontal, 1 mV vertical.

Injection (icv) of 15 nmol N-glycated GLP-1 enhanced long-term potentiation (LTP) compared with control. These results demonstrate [Nglyc]GLP-1 has direct and acute modulating effects on synaptic transmission and can enhance the induction of LTP.

Example 7

In vivo Effects of Treatment with Pro(9)GLP-1

Male Wistar rats were icv injected with either vehicle (Control,) or 15 nmol Pro(9)GLP-1 (♦). LTP was induced 30 min post-injection using the HFS (weak protocol), and the change in EPSP assessed and graphed to represent the change in LTP. A two-way repeated measures ANOVA showed a difference between the drug group and control (p<0.001). All groups n=6. Averaged EPSPs are shown recorded 5 min pre-tetanus and 1 h post-tetanus. Calibration bars are 10 ms horizontal, 1 mV vertical.

Injection (icv) of 15 nmol Pro(9)GLP-1 enhanced long-term potentiation (LTP) compared with control. These results demonstrate that Pro(9)GLP-1 has direct and acute modulating effects on synaptic transmission and can enhance the induction of LTP.

Example 8

In vivo Effects of Treatment with the GLP-1 Derivative, Liraglutide

Male Wistar rats were icv injected with either vehicle (Control,) or 15 nmol Liraglutide (♦). LTP was induced 30 min post-injection using the HFS (weak protocol), and the change in EPSP assessed and graphed to represent the change in LTP. A two-way repeated measures ANOVA showed a difference between the drug group and control (p<0.005). All groups n=6. Averaged EPSPs are shown recorded 5 min pre-tetanus and 1 h post-tetanus. Calibration bars are 10 ms horizontal, 1 mV vertical.

Injection (icv) of 15 nmol of the GLP-1 derivative, Liraglutide enhanced long-term potentiation (LTP) compared with control. These results demonstrate that Liraglutide has direct and acute modulating effects on synaptic transmission and can enhance the induction of LTP.

The results of the present study also show that the facilitating effects of GLP-1, and analogues thereof, on synaptic plasticity can prevent the detrimental effects that βA(25-35) fragments have on LTP. The fact that Val(8)GLP-1 has to be applied before beta-amyloid makes it unlikely that both compounds act at the same binding sites on neurons. Instead, it appears that the activation of GLP-1 receptors triggers mechanisms that prime synapses for increased LTP and prevent or counteract the effects that beta-amyloid has on synaptic plasticity by altering VDCC and other ion channel activity. Val(8)GLP-1 might elevate cAMP levels in neurons in a similar way that it increases cAMP levels in pancreatic beta cells. The Val(8)GLP-1 induced cAMP increase then could enhance vesicle release in this fashion and make synaptic activity less dependent on VDCC activity, which is affected by beta-amyloid. VDCC activity would ordinarily be required to enhance cAMP levels via Ca2+ sensitive nucleotide cyclases, and this step could be circumvented by the Val(8)GLP-1 action. Since the chronically increased activation of Ca2+ channels leads to neurotoxic processes such as the increased production of free radicals, the observation that GLP-1 receptor activation prevents the effects of beta-amyloid holds the great promise that the early degenerative effects of beta-amyloid can be reduced, and the downstream processes that lead to neurodegeneration can be prevented. In addition, the growth factor-like effects that GLP-1 has on neurons by increasing dendritic sprouting and neuronal regeneration could help prevent or reduce long-term damage induced by beta-amyloid activity and plaque-induced gliosis. These properties of GLP-1, and analogues thereof, suggest that the treatment of AD patients with stable GLP-1 analogues could be an effective prophylactic treatment of Alzheimer's disease.

In conclusion, the properties of GLP-1 analogues described herein, suggest that the treatment of subjects with stable GLP-1 agonists could be an effective prophylactic treatment of neurological disorders caused by, or associated with, impaired LTP.

The invention claimed is:

1. A method of improving memory in a subject comprising administering to the subject a pharmaceutically acceptable amount of a peptide analogue of glucagon-like peptide-1 (7-36) selected from the group consisting of a peptide analogue 10 to 31 amino acids in length and comprising at least the first 10 amino acids from the N-terminal end of the sequence identified in SEQ ID NO: 1; a peptide analogue 10 to 31 amino acids in length comprising at least the first 10 amino acids from the N-terminal end of the sequence identified in SEQ ID NO: 1 and further comprising N-terminal glycation; a peptide consisting of the sequence identified in SEQ ID NO: 1; a peptide consisting of SEQ ID NO:1 with N-terminal glycation; a peptide analogue 10 to 31 amino acids in length and comprising at least the first 10 amino acids from the N-terminal end of the sequence identified in SEQ ID NO:2 wherein $X_1$ is selected from L-His and D-His, $X_2$ is selected from L-Val and D-Val, and $X_3$ is selected from L-Glu and D-Glu; a peptide analogue consisting of the sequence identified in SEQ ID NO: 4; a peptide analogue 10 to 31 amino acids in length and comprising at least the first 10 amino acids from the N-terminal end of the sequence identified in SEQ ID NO:2 wherein $X_1$ is selected from L-Asp and D-Asp, $X_2$ is selected from L-Ala and D-Ala, and $X_3$ is selected from L-Glu and D-Glu; a peptide analogue consisting of the sequence identified in SEQ ID NO: 3; a peptide analogue 10 to 31 amino acids in length and comprising at least the first 10 amino acids from the N-terminal end of the sequence identified in SEQ ID NO:2 wherein $X_1$ is selected from L-His and D-His, $X_2$ is selected from L-Ala and D-Ala, and $X_3$ is selected from L-Pro and D-Pro; a peptide analogue consisting of the sequence identified in SEQ ID NO: 5; a peptide analogue 10 to 31 amino acids in length and comprising at least the first 10 amino acids from the N-terminal end of the sequence identified in SEQ ID NO:2, wherein $X_2$ is Ala or Val and wherein the peptide analogue further comprises addition of L-Glu, D-Glu, or addition of a C-16 palmitoyl fatty acid at Lys(20), or an amino acid substitution by L-Arg or D-Arg at Lys(28) of SEQ ID NO:2; and a peptide analogue Arg(34)Lys(26)-(N-epsilon-(gamma-Glu) (N-alpha-hexadecanoyl))GLP-1(7-37).

2. The method according to claim 1, wherein the amino acid sequence of the peptide analogue consists of the sequence identified in SEQ ID NO: 1.

3. The method according to claim 1, wherein the peptide analogue further comprises N-terminal glycation.

4. The method according to claim 2, wherein the peptide analogue further comprises N-terminal glycation.

5. The method according to claim 1 wherein the peptide analogue is 10 to 31 amino acids in length and the amino acid sequence of the peptide analogue comprises at least the first 10 amino acids from the N-terminal end of the sequence identified in SEQ ID NO:2 wherein $X_1$ is selected from L-His and D-His, $X_2$ is selected from L-Val and D-Val, and $X_3$ is selected from L-Glu and D-Glu.

6. The method according to claim 1, wherein the amino acid sequence of the peptide analogue consists of the sequence identified in SEQ ID NO: 4.

7. The method according to claim 1 wherein the peptide analogue is 10 to 31 amino acids in length and the amino acid sequence of the peptide analogue comprises at least the first 10 amino acids from the N-terminal end of the sequence identified in SEQ ID NO:2 wherein $X_1$ is selected from L-Asp and D-Asp, $X_2$ is selected from L-Ala and D-Ala, and $X_3$ is selected from L-Glu and D-Glu.

8. The method according to claim 1, wherein the amino acid sequence of the peptide analogue consists of the sequence identified in SEQ ID NO: 3.

9. The method according to claim 1 wherein the peptide analogue is 10 to 31 amino acids in length and the amino acid sequence of the peptide analogue comprises at least the first 10 amino acids from the N-terminal end of the sequence identified in SEQ ID NO:2 wherein $X_1$ is selected from L-His and D-His, $X_2$ is selected from L-Ala and D-Ala, and $X_3$ is selected from L-Pro and D-Pro.

10. The method according to claim 1, wherein the amino acid sequence of the peptide analogue consists of the sequence identified in SEQ ID NO: 5.

11. The method according to claim 1 wherein the peptide analogue is 10 to 31 amino acids in length and the amino acid sequence of the peptide analogue comprises at least the first 10 amino acids from the N-terminal end of the sequence identified in SEQ ID NO:2, wherein $X_2$ is Ala or Val; and wherein the peptide analogue further comprises addition of L-Glu, D-Glu, or addition of a C-16 palmitoyl fatty acid at Lys(20), or an amino acid substitution by L-Arg or D-Arg at Lys(28) of SEQ ID NO:2.

12. The method according to claim 1, wherein the peptide analogue is Arg(34)Lys(26)-(N-epsilon-(gamma-Glu) (N-alpha-hexadecanoyl))GLP-1(7-37).

\* \* \* \* \*